(12) United States Patent
Tweardy et al.

(10) Patent No.: US 6,921,376 B2
(45) Date of Patent: Jul. 26, 2005

(54) CERVICAL BRACE

(75) Inventors: Lisa A. G. Tweardy, Thalwil (CH);
Will Pickering, Brooklyn, NY (US);
Clay Burns, New York, NY (US)

(73) Assignee: The Jerome Group, Inc., Moorestown, NJ (US)

( * ) Notice: Subject to any disclaimer, the term of this patent is extended or adjusted under 35 U.S.C. 154(b) by 0 days.

(21) Appl. No.: 10/001,451

(22) Filed: Oct. 23, 2001

(65) Prior Publication Data

US 2003/0078529 A1 Apr. 24, 2003

(51) Int. Cl.[7] .................................................. A61F 5/00
(52) U.S. Cl. ................................. 602/18; 128/DIG. 23
(58) Field of Search ............................. 602/17, 18, 19; 128/DIG. 23

(56) References Cited

U.S. PATENT DOCUMENTS

| 2,820,455 | A | * | 1/1958 | Hall ............................. 602/18 |
| 2,904,040 | A | * | 9/1959 | Hale ............................. 602/18 |
| 4,502,471 | A | | 3/1985 | Owens |
| 4,582,051 | A | * | 4/1986 | Greene et al. ................. 602/18 |
| 4,677,969 | A | * | 7/1987 | Calabrese ..................... 602/18 |
| 4,913,135 | A | * | 4/1990 | Mattingly .................... 602/18 |
| 5,201,702 | A | * | 4/1993 | Mars ........................... 602/17 |
| 5,531,669 | A | | 7/1996 | Varnau |
| 5,575,763 | A | | 11/1996 | Nagata et al. |
| 5,624,387 | A | | 4/1997 | McGuinness |
| 5,637,067 | A | | 6/1997 | Ausmus |
| 5,776,088 | A | | 7/1998 | Sereboff |
| 5,964,722 | A | | 10/1999 | Goralnik et al. |
| 6,045,522 | A | | 4/2000 | Grober |
| 6,213,765 | B1 | | 4/2001 | Standerwick et al. |
| 6,267,741 | B1 | * | 7/2001 | Lerman ............... 128/DIG. 23 |
| 6,315,746 | B1 | * | 11/2001 | Garth et al. ................... 602/18 |
| 6,733,469 | B2 | * | 5/2004 | Miyaji et al. ................. 602/18 |

* cited by examiner

Primary Examiner—Michael A. Brown
Assistant Examiner—Fenn C. Mathew
(74) Attorney, Agent, or Firm—Schnader Harrison Segal & Lewis LLP

(57) ABSTRACT

The present invention provides a cervical brace that has a chest plate secured to the thorax of a wearer and a chin strut attached to the chest plate. In a preferred embodiment, the chin strut extends to a point on a chin support of a cervical collar disposed adjacent a wearer's chin so as to provide better support. The chest plate is in the form of a vest or can be comprised of a chest plate and a back plate. In preferred embodiments the chin strut extends in a straight line from the chest plate to the chin support and is adjustable and maybe positioned securely, relative to the chest plate, the cervical brace also has a back plate and an occipital support. In certain embodiments it has a rear strut extending between the occipital support and the back plate. In such embodiments, the back plate and the chest plate are preferably attached to each other around the body. In accordance with one aspect of the present invention, the rear strut is adjustable and further has a strut latch, which is most preferably an eccentric lever for locking one end of the rear strut to a bracket affixed to the back plate. In another embodiment it may have a strap which serves the occipital support to the forehead.

23 Claims, 10 Drawing Sheets

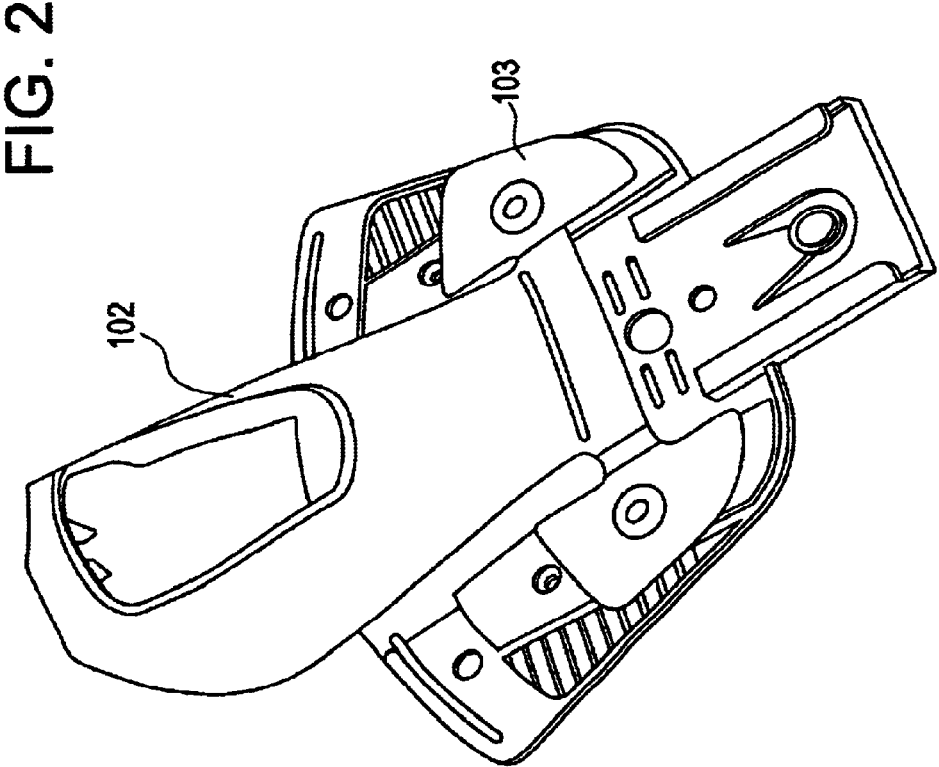

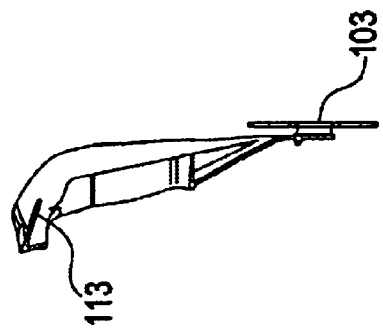
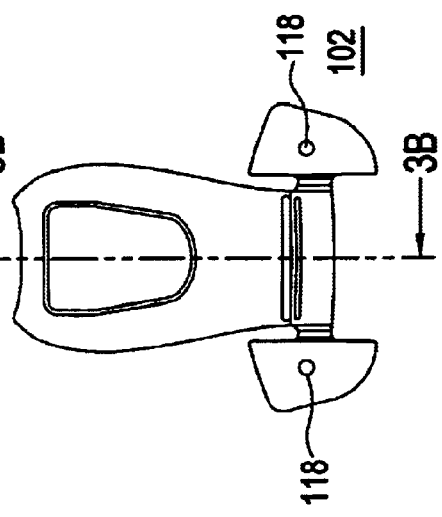
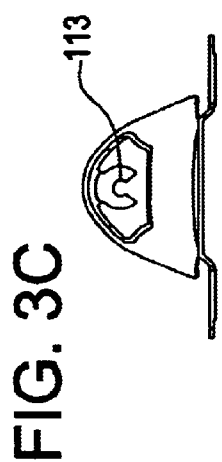
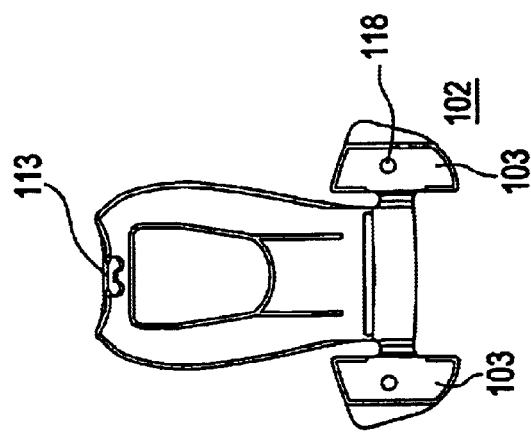

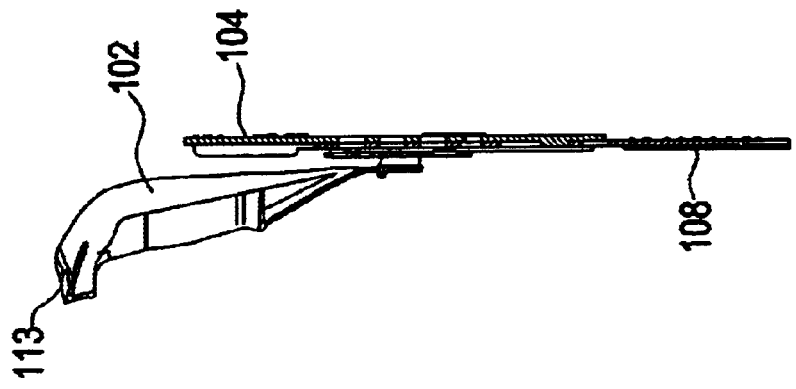
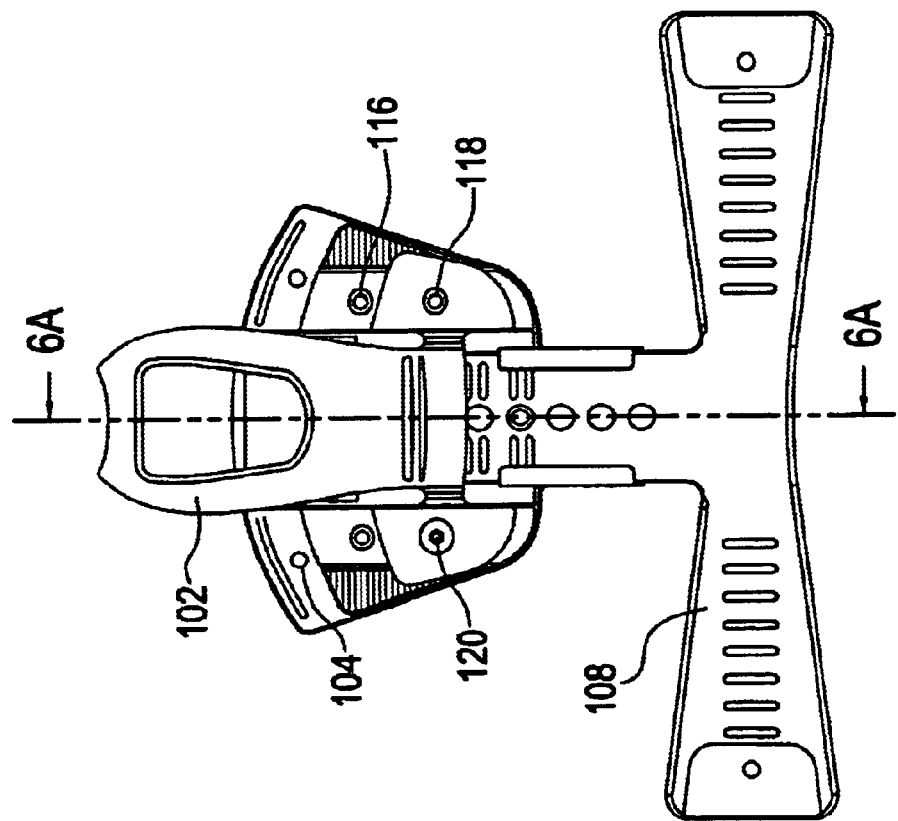

CERVICAL BRACE

TECHNICAL FIELD

The present invention relates, in general, to orthopedic units and, in particular, to cervical collars and/or cervical thoracic orthoses.

BACKGROUND OF THE INVENTION

Various cervical thoracic orthoses have been developed for treating cervico-thoracic injuries of the upper thoracic spine and lower cervical spine. Some of these are collars which function to partially immobilize the head and neck of the patient and relieve spasm or strain by transferring load or force from the head of a patient to the shoulders or adjacent areas of the patient. Other devices designed for complete or near complete immobilization of the head and neck of the patient have also been developed.

A feature, preferably included in cervical thoracic orthoses to overcome limited adaptability or to accommodate the body of the patient and the particular ailment prompting the need for wearing an orthosis, is the facility for adjusting the relative positions of various components of the cervical thoracic orthosis. Currently available orthoses generally lack such features.

Various types of cervical thoracic orthoses have been developed in treating conditions of the cervical spine, cervico-thoracic junction (i.e. the upper thoracic spine and lower cervical spine) or occipital-cervical junction (i.e. occiput to upper cervical spine). Some of these are collars which are intended merely where support for the head and neck is needed. The primary objective for the use of such a collar is to partially immobilize the head and neck, to maintain a desired spinal alignment, to provide support for the head, and to relieve any spasm or strain to which the neck muscles may be subjected by transmitting load or force from the head to the shoulders or adjacent area. Other collars are intended for use where near complete immobilization of the head and neck are necessary such as when a patient is attended to by emergency medical personnel prior to admission to a hospital. There are a multitude of cervical collars intended to perform one or more of the above-mentioned functions.

U.S. Pat. No. 5,776,088—Sereboff describes an adjustable, flexible cervical collar designed for universal use by providing vertically adjustable movable sections that support the chin and the back of the head, which can also be displaced around the circumference of the collar.

Other collars intended for partial or total immobilization are shown in U.S. Pat. Nos. 4,502,471—Owens and U.S. Pat. No. 4,582,051—Greene et al. Both these collars attempt to provide stability by providing a front and rear brace that connects a collar to a lower section that either rests on the patients shoulders or is a belt surrounding the thorax. A more elaborate version of such a brace is disclosed by U.S. Pat. No. 5,531,669—Vamau, which has adjustable pads to support the chin and the occipit, that are in turn supported by flexible and vertically adjustable members that are attached to a vest that is fitted over the shoulders and which has a strap that surrounds the thorax.

Other prior art devices include cervical orthosis or a brace that restrains the head from movement by a band attached to the forehead of the patient, which is then restrained by connecting the band to the shoulders or upper thorax. Such a device is shown in U.S. Pat. No. 5,624,387—McGuiness, which uses a set of adjustable rods and bars to effect stabilization. Another device in this category is shown in U.S. Pat. No. 5,575,763—Nagata et al., which discloses restraint and stabilization using an integral molded device that can only be fitted within narrow ranges of adjustment.

Thus there remains a long-felt yet unmet need for a cervico-thoracic orthosis that can be easily adjusted to provide a variable support length from the point of the chin to the sternum, and also for a brace that can support the occipital region in a similarly adjustable and most importantly a brace that can easily adapt to the wide variety of patient phenotypes that exist, without the need for extensive customization.

SUMMARY OF THE INVENTION

The present invention provides a cervical brace that has a chest plate secured to the thorax of a wearer and a chin strut attached to the chest plate. In a preferred embodiment, the chin strut extends to a point on a chin support of a cervical collar disposed adjacent a wearer's chin so as to provide better support. The chest plate is in the form of a vest or can be comprised of a chest plate and a back plate. In preferred embodiments the chin strut extends in a straight line from the chest plate to the chin support and is adjustable and may be positioned securely relative to the chest plate. The cervical brace also has a back plate and an occipital support. In certain embodiments, it has with a rear strut extending between the occipital support and the back plate. In such embodiments, the back plate and the chest plate are preferably attached to each other around the body. In accordance with one aspect of the present invention, the rear strut is adjustable and further has a strut latch, which is most preferably an eccentric lever for locking one end of the rear strut to a bracket affixed to the back plate. In another embodiment it may have a strap which secures the occiptal support to the forehead.

Thus, the present invention discloses a cervical brace that has a cervical collar with front and rear portions, where the rear portion has an occipital support, and also includes a vest and a rear strut extending between the occipital support and the vest and also includes a head strap. The rear strut preferably has a rear strut latch to adjust the relative position of said rear strut, and this latch is most preferably formed by the latch mechanism and latch housing being disposed on the rear strut. In certain preferred embodiments, the latch has an eccentric element that moves into and out of engagement with a locking mechanism, so that the angle of the rear strut relative to the rear portion may be adjusted, as can the distance between the occipital support and the vest. This feature is preferably effected by having a latch housing comprising one or more receiving elements that engage the latch to adjust the relative distance between the cervical collar and the vest, and these receiving elements preferably comprise corresponding serrated surfaces that move into and out of engagement upon rotation of the latch relative to the housing. The latch housing preferably has one or more extensions and the vest has one or more locking slots, so that the extensions and locking slots engage the rear strut with the vest. In certain embodiments, a head strap extending from said occipital support is also provided.

Methods of supporting the cervical spine of an injured patient are also disclosed, wherein a cervical collar is attached to the patient and a chin strut is positioned from an edge of the cervical collar adjacent the chin of the patient to a chest plate, and then adjusting the relative position of the head by selecting a relative position between the chin strut and the chest plate. Next a chest plate is attached to the patient's thorax and the chin strut affixed thereto. Additionally, for some patients, an occipital support is attached to the patient and a rear strut to the occipital support. A back plate is then also attached to the patient and the rear strut is adjusted and locked to the back plate.

BRIEF DESCRIPTION OF THE DRAWINGS

FIG. 2 is a plan view of the anterior sub-assembly shown in FIG. 1A and further illustrating the components thereof;

FIGS. 3A–3E are a set of orthographic views of a chin strut made in accordance with the present invention;

FIGS. 6–6A are a set of orthographic views illustrating an anterior subassembly as shown in FIG. 2, incorporating the chin strut shown in FIGS. 3A–3E and the upper and lower anterior front plates seen in FIGS. 4–5;

DETAILED DESCRIPTION OF THE PREFERRED EMBODIMENTS

Figure 1A:
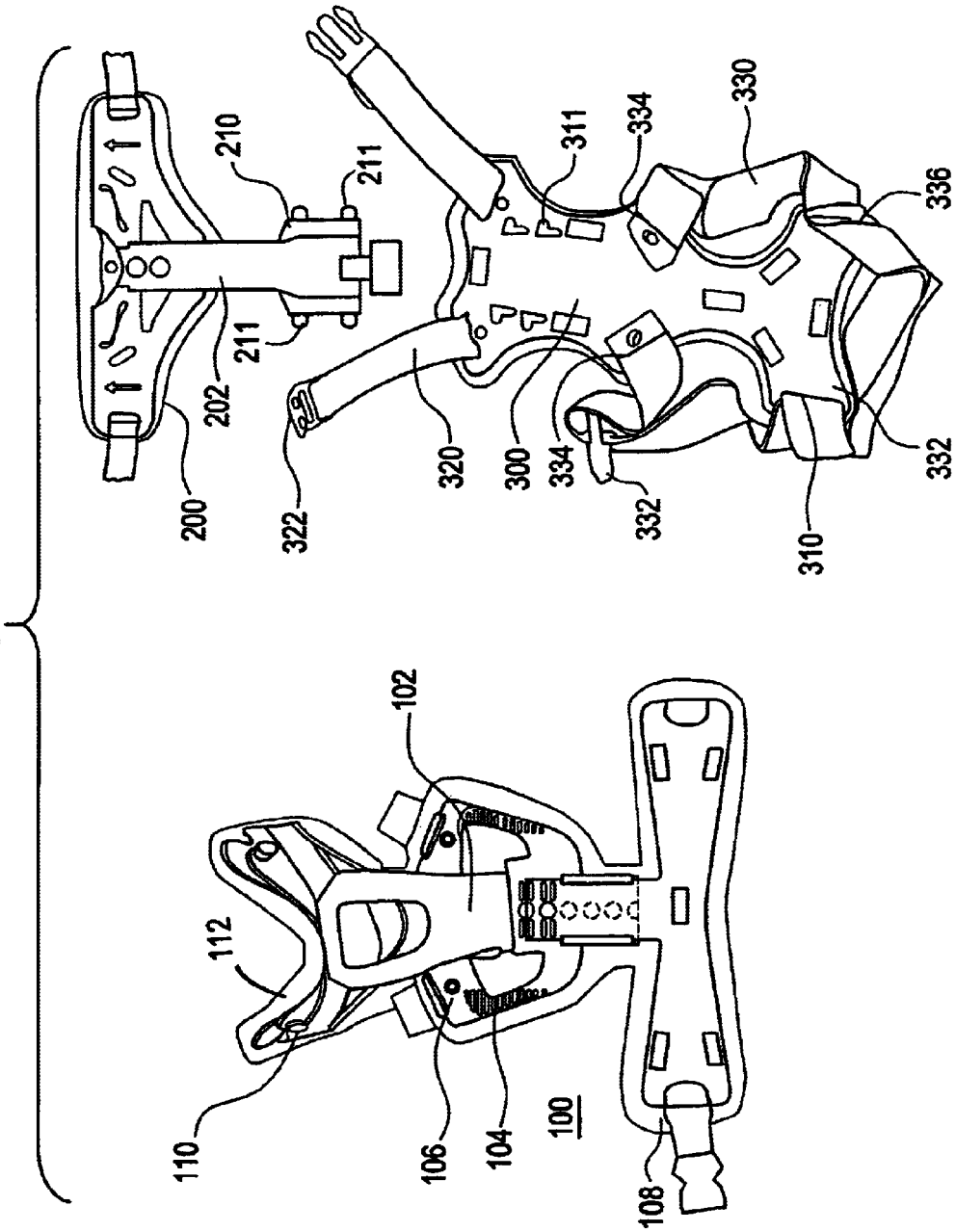
FIG. 1A is a plan view of the sub-assemblies that together make up a preferred embodiment of the cervical collar of the present invention.
Figure 1B:
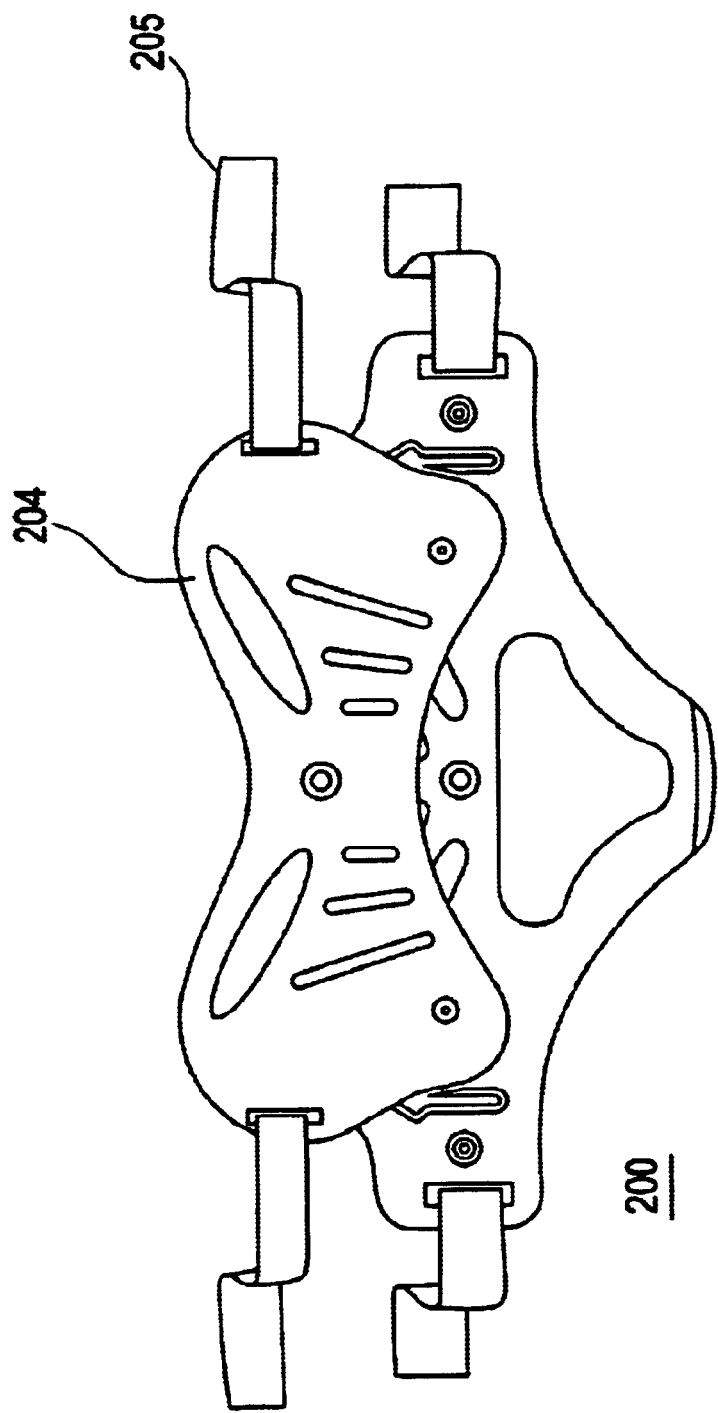
FIG. 1B is a plan view of the posterior portion of a cervical collar used in the present invention.

Referring now to FIG. 1A and FIG. 1B, there is shown a plan view of the elements that comprise an overall preferred assembly of a cervical collar made in accordance with the present invention. A padded cervical collar 110 is supported by an anterior assembly 100, which is comprised of a chin strut 102 and an anterior plate assembly 104. The anterior plate assembly 104 is itself preferably comprised of two pieces: an upper front plate 106 and a lower front plate 108. A posterior assembly 200 is similarly comprised of an occipital support 204 and a molded back plate 300. Finally, a rear strut 202 and/or a head strap 205 is provided in certain embodiments. Occipital support 204 and head strap 205 have been omitted from posterior assembly 200 in FIG. 1A so that strut 202 may be seen more easily. When assembled and worn, these elements provide a collar that supports the middle of the cervical spine exceptionally well and which has all the features and advantages described below.

Figure 4:
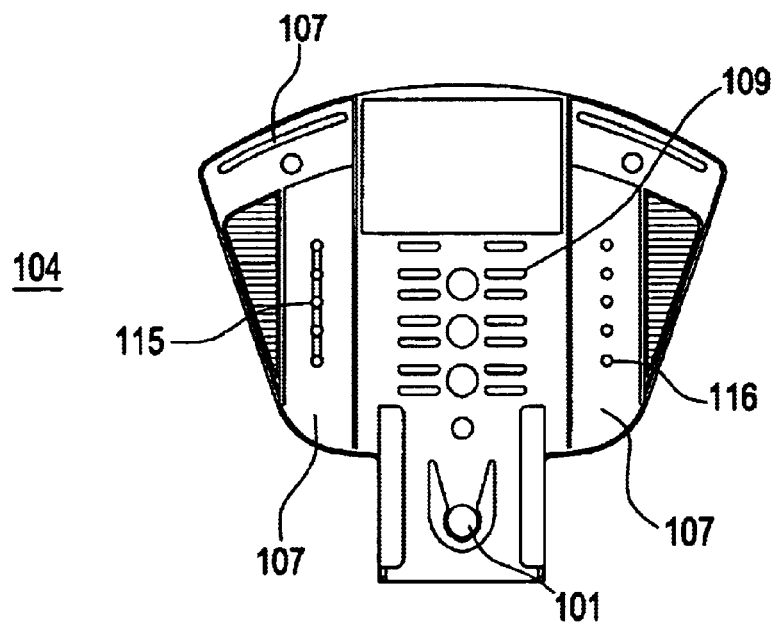
FIG. 4 is a plan view of an upper anterior front plate seen in FIG. 2.

As will be further appreciated by those familiar with such device, the design of the anterior assembly of the present invention is also well-suited to support and accommodate injuries to the cervical thoracic junction, that is, injuries to the region of the lower cervical spine and the upper thoracic spine, while the design of the posterior assembly, in particular with a head strap 205 provides support for patients with upper cervical spinal injury. Further details of the anterior assembly are illustrated in FIGS. 2–6. As seen in FIG. 2, the chin strut 102 is most preferably provided with an adjustable affixation section 103, which most preferably is a hook-and-loop type fastener, although other types of fasteners or structures may be provided. Additional details of the chin strut 102 can be appreciated through review of FIGS. 3A–3D. FIG. 3A is a plan view of a chin strut and FIG. 3B is a cross-sectional elevation view taken at line B—B in FIG. 3A, and illustrates the adjustable affixation section 103 that is preferably disposed on a relatively flat and relatively flexible surface so that it may adjustably cooperate with the upper front plate 106 shown in FIG. 4. The chin strut 102 is preferably a contoured molded structure that extends upward toward the chin and includes an attachment point 113 that cooperates with the cervical collar 110. In a preferred embodiment, the attachment point 113 is designed to cooperate with existing elements of the cervical collar 110 so that no separate fastener is needed to affix these two subassemblies. Chin strut 102 is preferably attached to cervical collar chin support 112, as shown in FIG. 1A. In this manner, the cervical collar 110 is attached to the anterior assembly in a manner that limits the movement of the chin upward and downward, as well as sideways and rotationally, and thereby stabilizes the wearer since the chin strut 102 is designed to have sufficient rigidity and stiffness to provide such stability. In accordance with the present invention, the chin strut 102 preferably supports the chin of the wearer and transfers force from this point directly to the sternum, rather than the chin of the wearer being supported only by the padded cervical collar 110. Chin strut 102 may be affixed to upper front plate 106 by hook and loop fasteners as herein above described, or by some other appropriate means. As an example, upper front plate 106 can include an elongated slot 115 as shown in FIG. 4, for receiving a rivet 120 in chin strut 102. For this purpose, chin strut 102 includes hole 118. In this manner, chin strut 102 can slide along elongated slot 115. Alternatively, upper front plate 106 may include a series of holes 116, whereby once the correct position for chin strut 102 is determined, plastic rivets can be used through holes 116 and 118 to secure upper front plate 106 to chin strut 102.

Figure 5:
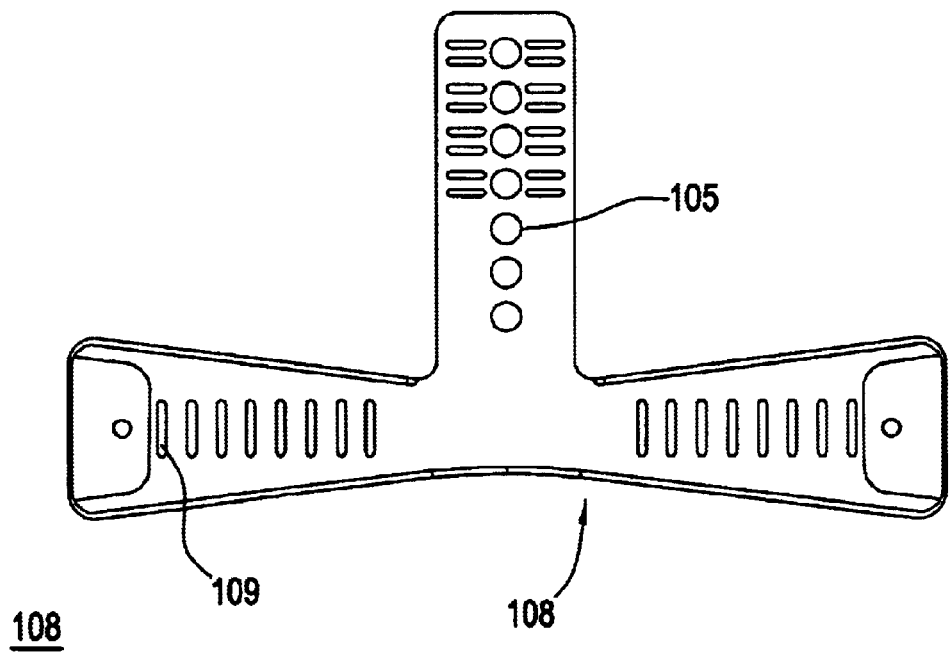
FIG. 5 is a plan view of a lower anterior front plate seen in FIG. 2.

Referring now to FIGS. 4–5, plan views of the upper front plate 106 and lower front plate 108 that preferably make up the anterior plate assembly 104 are shown. As seen in FIG. 4, the upper front plate 106 preferably includes affixation sections 107 that are designed to cooperate with the affixation section 103 described above with reference to the chin strut 102. If, as described with reference to the chin strut, a hook-and-loop fastener is employed, the affixation sections 107 would be designed and placed to be in a corresponding relationship with the affixation sections 103 when the chin strut 102 and the upper front plate 106 are brought together in an assembly and would include complementary hook-and-loop fasteners. Numerous other types of fasteners could be used, either integrally molded or formed as part of these components, or provided as separate pieces, so long as the upper front plate 106 or other corresponding structure could be removably and adjustably attached to the chin strut 102 to effect the stabilization function described above.

FIGS. 4 and 5 also illustrate a series of affixation points 105 that are used in to affix these two elements in a pre-determined relationship that is selected based upon the size of the wearer, the orientation of the head and neck, and other criterion familiar to those who use and apply cervical collars and cervical thoracic orthoses. An additional affixation point 101 (seen in FIG. 4) is preferably provided so that the anterior plate assembly 104 of the upper front plate 106 and the lower front plate 108 adjustably secured after assembly, this particular affixation point 101 is also used to affix the chin strut 102 to the overall anterior assembly 100, as explained in further detail below. The upper and lower anterior plates 106, 108 also include slots 109 for attaching securing straps, which are illustrated in FIG. 1A. Both the upper and lower front plates 106,108 also preferably molded from or die cut from a sheet of relatively flexible and strong plastic material, although any suitable material known to those in the art may be utilized. Although not illustrated, it is further understood by those of skill in the art that the components discussed with reference to FIGS. 4 and 5 can include padding or surfacing materials for patient comfort, or other purposes.

The subassembly described above with reference to FIGS. 1–2 is further illustrated in FIGS. 6 and 6A where the arrangement of the components described with reference to FIGS. 3–5 is illustrated. As explained above, the adjustable affixation points 101,105 are disposed so that upon assembly in proper alignment, the two portions can be adjusted and snapped or affixed together using any of a number of techniques and structures well known in the art. Lower front plate 108 is slidably engaged in upper front plate 106. Affixation point 101 is a button biased outwardly which locks into an affixation point 105 to secure lower front plate 108 per front plate 106. Upon completing this assembly process, the chin strut 102 is added to complete the anterior plate assembly 104. The preferred embodiment of the present invention illustrated permits the wearer or the person applying the cervical brace to the wearer to adjust the relative dimensions between the chin strut 102 and the placement of the anterior plate assembly at a comfortable and appropriate location on the thorax of the patient so that the force is adequately transferred and stability is maintained. Further adjustment of lower front plate 108 per front plate 106 is also facilitated to accommodate patients of different body types. As explained in further detail below, the anterior plate assembly 104 and the lower plate 108 are each adapted to receive straps or similar affixation elements that permit the entire cervical brace to be comfortably and securely fitted to the patient.

Figure 7:
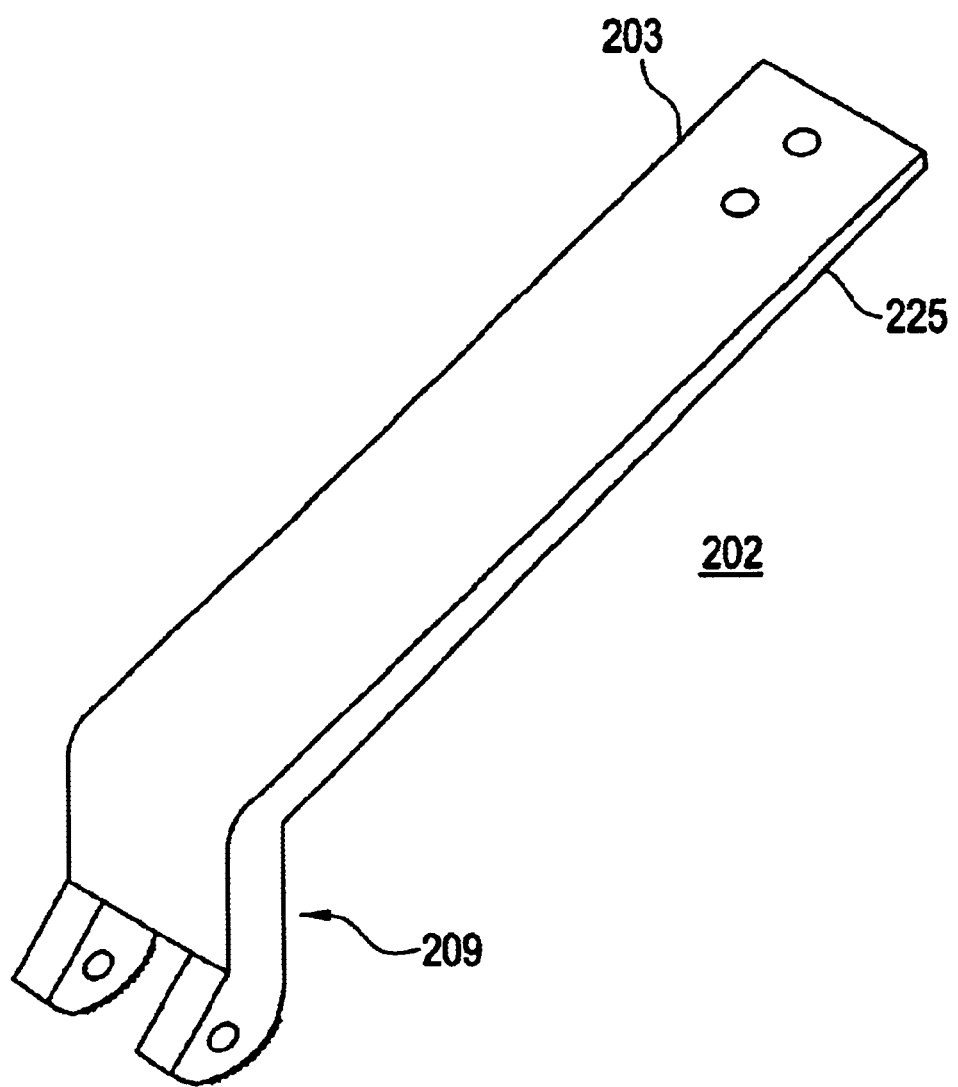
FIG. 7 is a perspective view illustrating the posterior strut assembly seen in FIG. 1A

Referring back to FIG. 1A, it was mentioned that a rear strut 202 is provided to connect the occipital support 204 of cervical collar 110 to the rest of the brace. The one end of the rear strut 202 is connected to an occipital support 204 that may include a head strap 205 that is used in certain indications to provide additional support. Extending from this end of this sub-assembly is the rear strut 202. Rear strut 202, when used, connects directly to cervical collar 110, either at occipital support 204 or at another point on the rear of cervical collar 110. Further details of this aspect of the present invention are illustrated in FIG. 7 and as seen therein, in a preferred embodiment, the rear strut 202 is preferably a carefully engineered component that has a distal end 203 that cooperates with an occipital plate 206 that is most preferably adjustable via a mechanism such as the screw adjustment wheel 207 seen in FIG. 7. A further feature of a preferred embodiment is the incorporation of a defined flexure point 225 at the point at which the rear strut 202 joins the occipital plate 206. The proximal end 209 of the rear strut 202 is preferably constructed to permit rotation about a pivot point in a releasable fashion, as explained further below.

Figure 8:
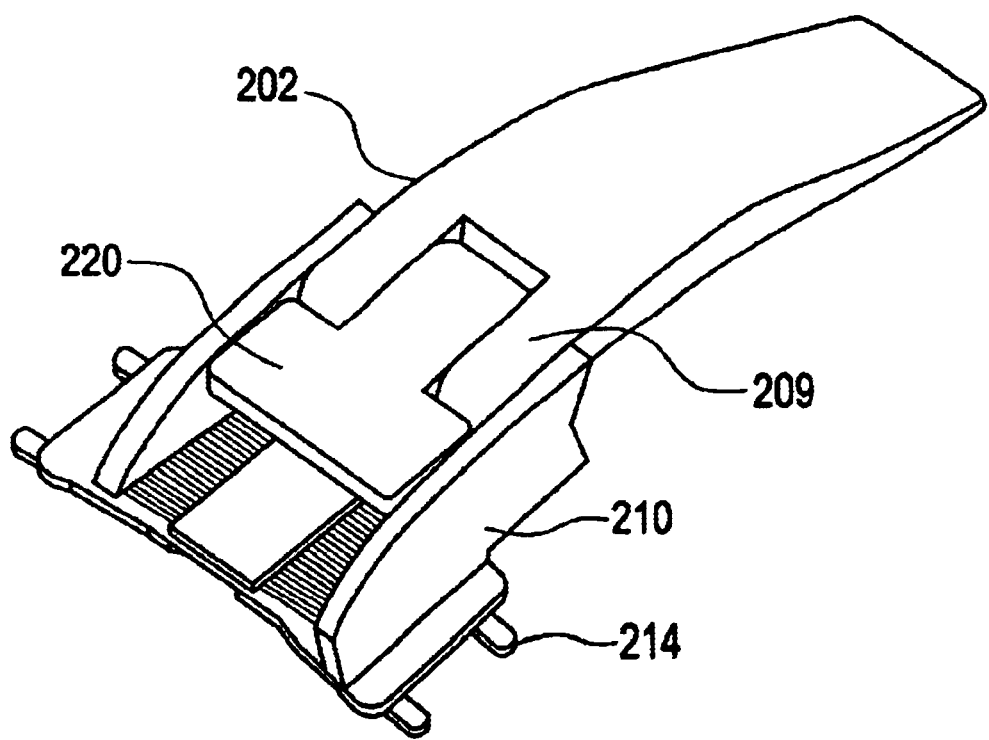
FIG. 8 is a perspective view, partially broken away of the posterior strut shown in FIG. 7.

Further details of the proximal end 209 of the rear strut 202 are illustrated in FIG. 8. As mentioned above, the rear strut 202 is permitted to rotate and, in a most preferred embodiment is also permitted to move vertically. As seen in FIG. 8 proximal end 209 of the rear strut 202 cooperates with a rear strut housing 210, and is held in place by the operation of a rear strut latch 220, the details of which are explained below. The rear strut housing 210 preferably includes extensions 214 or other cooperating elements that permit it to be easily attached to the molded back plate 300, which is shown in FIG. 1A and the further details of which are described below.

Figure 9:
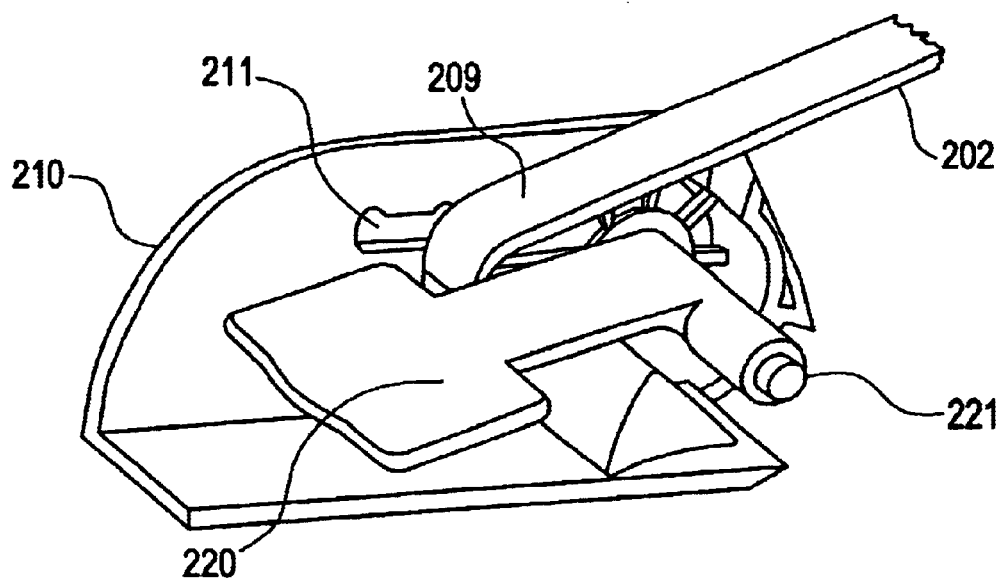
FIGS. 9–10 are two perspective views, partially cut away, of the latch shown in FIG. 8, illustrating respectively the locked and unlocked positions.
Figure 10:
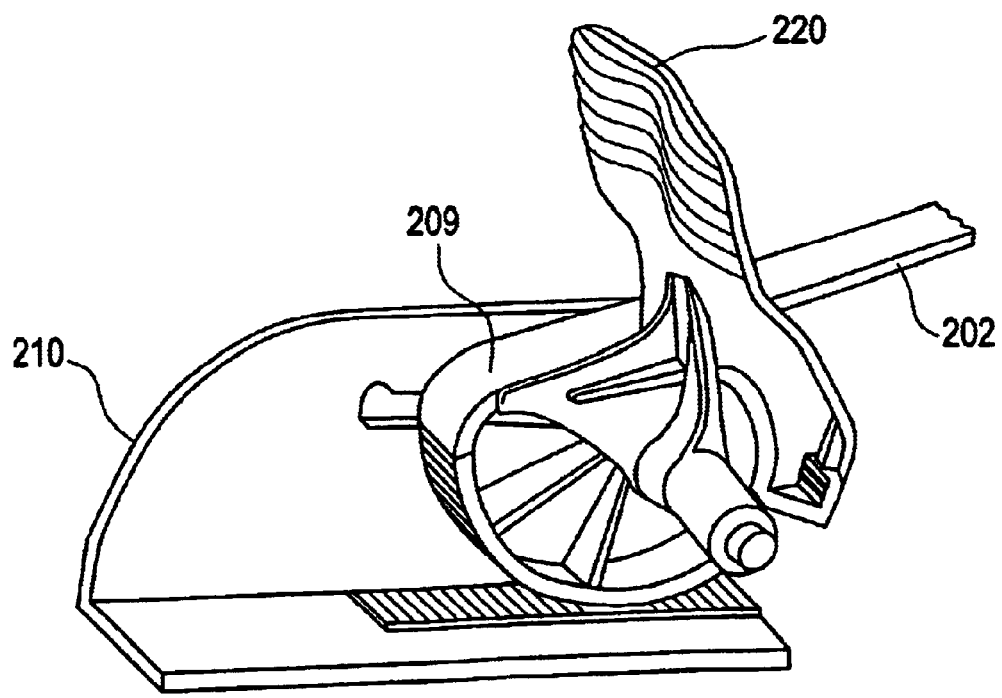
Figure 11:
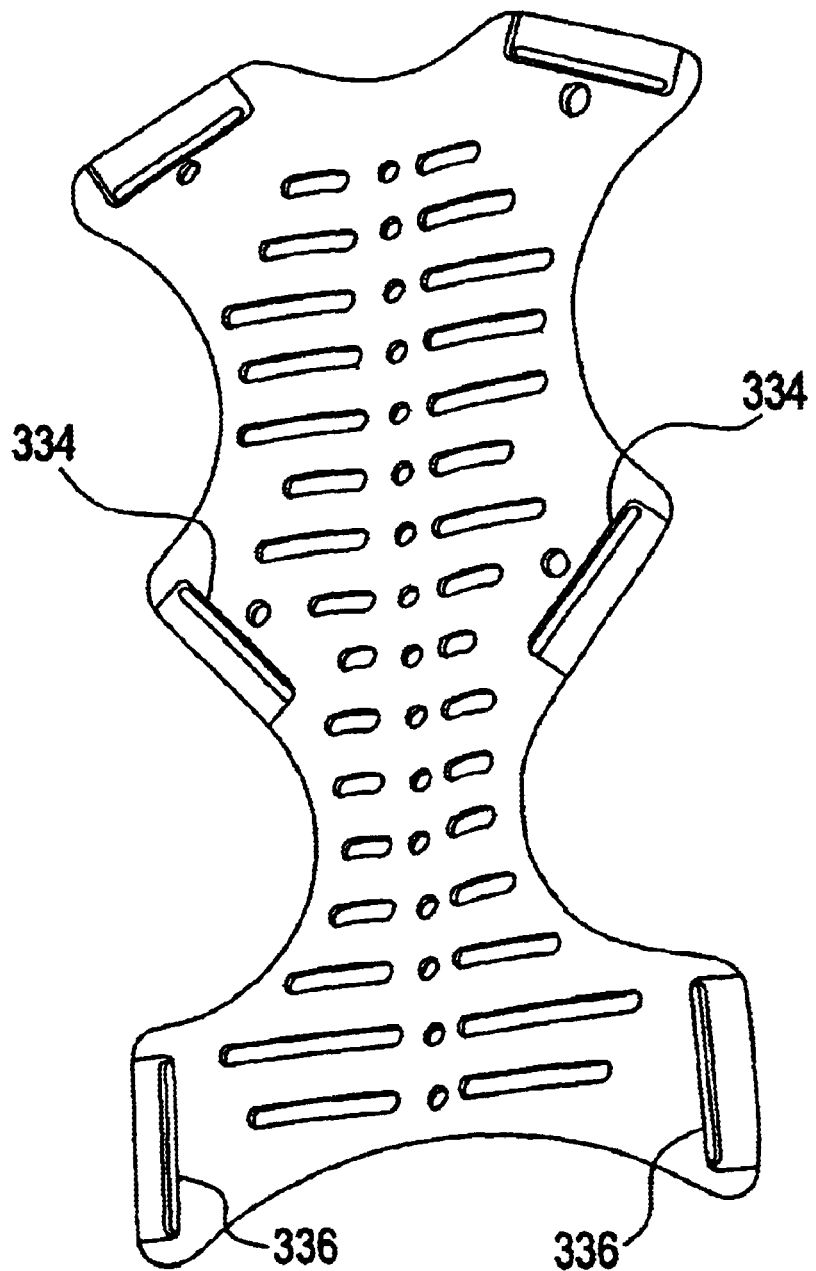
FIG. 11 is a plan view of the molded back plate of the present invention.

The construction and operation of the rear strut latch 220 is illustrated in FIGS. 9–10, which for the sake of clarity show a preferred embodiment of the present invention in which a portion of one side of the rear strut housing 210 has been cut away. Referring to FIG. 9, the cooperation of the rear strut housing 210 and the proximal end 209 of the rear strut 202 with the rear strut latch 220 can be appreciated. The rear strut latch 220 defines an axis of rotation 221 which cooperates with a receiving slot 211 that has a plurality of detents that together define a position for the axis of rotation 221 relative to the housing 210. It is due to the provision of this elongated receiving slot that the rear strut 202 may move relative to the point at which the rear strut housing is attached to the patient, and in this manner effect adjustability relative to the patient's head and rotational position of the head relative to the neck. The rear strut 202 is held firmly in place by the eccentric offset of the axis of rotation 221 so that when the rear strut latch 220 is raised, as shown in FIG. 10, the rear strut 202 is slightly elevated and free to move within the constraint provided by the engagement of ends of the axis of rotation 221 with the receiving slot 211. To further enhance the fixed position of the rear strut 202 when the rear strut latch 220 is closed or in the locked position, serrations 212 are provided, as are corresponding knurled surfaces 222 in the proximal end 209 of the rear strut 202. Although interlocking engagement between two sets of ridges, knurls or similar structures represents a preferred embodiment, those of skill in the art will appreciate that there are a number of other structures and techniques for obtaining a similarly secure locking engagement that can be freely substituted in this type of latching mechanism.

Referring again to FIG. 1A, a molded back plate 300 is also part of a preferred embodiment of the present invention. As explained above, the molded back plate 300 is comprised of a molded section 310 and a plurality of straps 320,330 for affixing the cervical collar assembly to the wearer. Upper straps 320 are disposed so that they engage co-operating latches or buckles 322 that are attached to the anterior assembly 100. Lower straps 330 surround the thorax and engage co-operating latches or buckles 332 that are also attached to the anterior assembly 100, and most preferably attached to the lower plate 108. Both upper straps 320 and lower straps 330 are adjustable. The manner of adjustability of straps 330 is important to the proper fitting of the cervical brace of the present invention as well as to the comfort of the wearer. Straps 330 are attached to molded back plate 300 at slots 334. Each strap 330 then passes through a buckle 332, and back to molded back plate 300 at slots 336. Strap 330 can then be attached to lower back plate 300 in any conventionally adjustable manner, such as by adjustable buckles. Strap 330 may also pass through slot 336 and then the end of strap 330 can be secured to another portion of strap 330 using hook and loop fasteners A further feature of the present invention is also visible with reference to FIG. 1A, namely the cooperation between the posterior assembly 200 and the molded back plate 300. As described above with reference to FIG. 8, the rear strut housing 210 preferably includes extensions 214 or other cooperating elements that permit it to be easily attached to the molded back plate 300. As illustrated in FIG. 1A, the molded back plate 300 also preferably includes receiving slots 311 that are adapted to accept and engage the extensions 214 of the rear strut housing 210 so that the posterior assembly 200 and the molded back plate 300 are locked together as the cervical brace of the present invention is fitted to the patient. As mentioned with reference to other aspects of the present invention, although the extensions 214 and receiving slots 311 represent a preferred embodiment of the present invention, other structures can be readily substituted.

Thus, it will be appreciated that upon assembly of the above-described components, a cervical brace capable of securely and comfortably supporting a patient suffering from any of a variety of cervical and cervico-thoracic injuries. One particular advantage of the design described herein is that the construction of the posterior strut transfers force from the base of the occiput to the rear of the thorax (the "back" colloquially) while still permitting height and angle to be adjusted. The design disclosed herein can be used in a modular manner; in other words, certain of the components described herein can be deleted from the overall assembly to create a specialized brace. For example, some patients may not need the head strap 205 described above. Similarly some patients may be adequately supported by an assembly that does not include the rear strut 202. Therefore, rear strut 202 may be used without head strap 205, and head strap 205 may be used without rear strut 202.

While there have been described preferred embodiments of the present invention, it should be obvious to those skilled in the art that various modifications and changes can be made without departing from the true spirit and scope of the invention.

What is claimed is:

1. A cervical brace for attachment to a cervical collar comprising:
    an anterior plate assembly adapted to be secured to the thorax of a wearer and having an upper front plate and a lower front plate wherein said upper front plate is adjustably attached to said lower front plate to accommodate wearers of different size and phenotypes; and
    a chin strut extending from a sternum area of said anterior plate assembly to a chin support of said cervical collar, wherein said chin strut has a detachable attachment point for attachment of said chin strut to said cervical collar.

2. The cervical brace of claim 1 wherein said chin strut is adjustably attached to said anterior plate assembly.

3. The cervical collar of claim 2, wherein adjustability is provided by attachment of said chin support and said anterior plate assembly using hook-and-loop fasteners.

4. The cervical brace of claim 1, further comprising a vest wherein said anterior plate assembly is a portion of said vest.

5. The cervical brace of claim 4, wherein said vest further comprises a back plate.

6. The cervical brace of claim 1, wherein said chin strut extends in a straight line from said sternum area of said anterior plate assembly to said chin support.

7. The cervical brace of claim 1, further comprising:
    a back plate adapted to be secured to the back of a the wearer;
    an occipital support; and
    a rear strut extending between said occipital support and said back plate.

8. The cervical brace of claim 7 further including straps for securing said back plate to said anterior plate assembly.

9. The cervical brace of claim 7 wherein said rear strut is adjustable and further comprises a strut lock.

10. The cervical brace of claim 9 wherein said strut lock comprises an eccentric lever for locking one end of said rear strut to a bracket affixed to said back plate.

11. A cervical brace comprising:
    a cervical collar having front and rear portions, wherein said rear portion comprises an occipital support;
    a vest comprising a front plate and a back plate;
    a rear strut extending between said occipital support and said back plate;
    a rear strut latch, whereby the relative position of said rear strut may be adjusted both angularly and vertically;
    a latch and latch housing disposed on said rear portion; and
    wherein said latch housing comprises one or more receiving elements that engage said latch to adjust the relative distance between said cervical collar and said vest.

12. The brace of claim 11, wherein said latch and latch housing comprise an eccentric element that moves into and out of engagement with a locking mechanism, whereby the angle of the rear strut relative to the rear portion may be adjusted.

13. The brace of claim 11, further comprising a head strap extending from said occipital support.

14. The brace of claim 11, wherein said latch housing comprises one or more extensions and the vest comprises one or more locking slots, whereby said extensions and said locking slots engage said rear strut with said vest.

15. A cervical brace for attachment to a cervical collar comprising:
    an anterior plate assembly adapted to be secured to the thorax of a wearer;
    a chin strut including means for attachment to said chest plate and means for attachment to a chin support of said cervical collar, said chin support to be disposed adjacent said wearer's chin;
    a back plate;
    an occipital support; and
    a rear strut extending between said occipital support and said back plate, wherein said rear strut is adjustable and includes a strut lock, and wherein said strut lock comprises an eccentric lever for locking one end of said rear strut to a bracket affixed to said back plate.

16. The cervical brace of claim 15 wherein said back plate is attached to said anterior plate assembly.

17. The cervical brace of claim 16 further comprising straps for securing said back plate to said anterior plate assembly.

18. The cervical brace of claim 15 wherein said rear strut includes means for independently adjusting the height and angle of attachment of said rear strut to said back plate.

19. A device comprising:
    a cervical collar having a chin support disposed beneath the chin of a wearer; and
    a cervical brace attached to the cervical collar;
    wherein the cervical brace comprises:
    a chest plate adapted to be secured to the thorax of said wearer;
    said chest plate having a portion disposed over the sternum of the wearer; and
    a chin strut extending from said sternum area of said chest plate to said chin support;
    said chin strut including means for attachment to said chest plate and detachable means for attachment to said chin support.

20. A cervical brace comprising:
    a cervical collar having front and rear portions, wherein said rear portion comprises an occipital support;

a vest comprising a front plate and a back plate;

a rear strut extending between said occipital support and said back plate;

a rear strut latch, whereby the relative position of said rear strut may be adjusted both angularly and vertically;

a latch and latch housing disposed on said rear portion;

wherein said latch housing comprises one or more receiving elements that engage the latch to adjust the relative distance between the cervical collar and the vest; and wherein said latch housing and said latch comprise corresponding serrated surfaces that move into and out of engagement upon rotation of said latch relative to said housing.

21. A method of supporting one of the cervical spine or upper thoracic spine of a patient comprising:

attaching a cervical collar having a chin support to the patient;

attaching a chin strut from said chin support of said cervical collar to an anterior plate assembly and adjusting the relative position of the head by selecting a relative position between said chin strut and said anterior plate assembly;

attaching said anterior plate assembly to the patient's thorax;

attaching an occipital support to the patient;

attaching a rear strut to said occipital support;

attaching a back plate to the patient;

adjusting said rear strut; and locking, with an eccentric lever, said rear strut to said back plate.

22. The method of claim 21 further comprising:

adjusting the vertical height of said anterior plate assembly independently of said adjustment of the relative position of said chin strut and said chest plate.

23. The method of claim 21 further comprising securing said back plate to said anterior assembly with straps.

* * * * *